(12) United States Patent
McConnell

(10) Patent No.: US 6,302,121 B1
(45) Date of Patent: Oct. 16, 2001

(54) DENTAL FLOSS DISPENSER

(75) Inventor: Mark Edward McConnell, Foster City, CA (US)

(73) Assignee: Gillette Canada Company (CA)

( * ) Notice: Subject to any disclaimer, the term of this patent is extended or adjusted under 35 U.S.C. 154(b) by 0 days.

(21) Appl. No.: 09/386,880

(22) Filed: Aug. 31, 1999

(51) Int. Cl.$^7$ ...................................... B26F 3/00
(52) U.S. Cl. ............................. 132/321; 225/44
(58) Field of Search ..................... 132/321, 324, 132/325; 206/63.5, 409, 408; 225/47, 39, 44, 56; 242/138

(56) References Cited

U.S. PATENT DOCUMENTS

| | | | |
|---|---|---|---|
| 337,852 | * 3/1886 | Meyers | 132/324 |
| 1,210,205 | * 12/1916 | Richardson | 132/324 |
| 4,925,073 | * 5/1990 | Tarrson et al. | 225/44 |
| 5,156,311 | 10/1992 | Spencer, Jr. et al. | 225/47 |
| 5,415,187 | * 5/1995 | Heneveld | 132/325 |
| 5,806,666 | 9/1998 | Chiang et al. | 206/635 |
| 5,823,207 | * 10/1998 | Bushman | 132/325 |
| 6,056,179 | * 5/2000 | Muzquiz | 225/47 |
| 6,189,545 | * 2/2001 | Tamez | 132/325 |

* cited by examiner

Primary Examiner—Todd E. Manahan
(74) Attorney, Agent, or Firm—David A. Howley

(57) ABSTRACT

A floss dispenser includes a housing that includes an exit, and a floss carrier disposed in the housing, where the floss carrier includes an arm extending across the exit, and a strand of dental floss on the floss carrier and extending through the exit.

19 Claims, 5 Drawing Sheets

DENTAL FLOSS DISPENSER

BACKGROUND OF THE INVENTION

The invention relates to dental floss dispensers.

The advantages of flossing on a regular basis have been well documented and dental floss has been widely sold and widely used. Dental floss is available in the form of a spool of dental floss housed in a dispenser. The dispensers permit a user to dispense a desired length of floss while storing the remainder of the unused floss.

Dental floss is dispensed from some dispensers by pulling a free end of the floss. As the user pulls on the floss, the spool rotates and the floss unwinds from the spool. During this process, the strand of floss can slip out of the exit hole of the dispenser and become stuck in the housing of the dispenser (e.g., between the walls of the dispenser), and fray or snag. The force with which the floss is pulled from the dispenser can also cause the spool of floss within the housing to unwind so rapidly that the floss becomes snagged and entangled inside of the dispenser housing.

SUMMARY OF THE INVENTION

In one aspect, the invention features a floss dispenser that includes a) a housing that includes an exit for floss, b) a floss carrier disposed in the housing, the floss carrier including an arm extending across the exit, and c) a strand of dental floss on the floss carrier, the strand extending through the exit. In one embodiment, the arm is positioned to maintain a strand of floss in the exit. In another embodiment, the arm defines a portion of the exit. In other embodiments, the arm includes an elbow.

In some embodiments, the housing further includes a finger extending from the housing toward the arm. In other embodiments, the dispenser further includes a nonreturn loading mechanism. In one embodiment, the nonreturn loading mechanism includes the arm and a finger extending from the housing toward the arm.

In other embodiments, the arm includes an elbow and the finger extends toward the elbow. In another embodiment, the arm and the finger are positioned to facilitate the loading of a strand of floss in the exit and to inhibit the strand of floss from leaving the exit. In some embodiments, the finger includes a tapered surface. The finger can be triangular in shape.

In one embodiment, the housing includes a unitary housing. In other embodiments, the housing includes a spindle and the floss carrier is disposed on the spindle. In another embodiment, the housing further includes a cutter and an opening disposed between the exit and the cutter, and a portion of the floss carrier is positioned in the opening. In some embodiments, the portion of the carrier positioned in the opening is transparent.

In other embodiments, the carrier includes a back wall and an arcuate side wall extending from the back wall. In one embodiment, the arcuate side wall includes an opening. In another embodiment, the back wall is substantially smooth. In another embodiment, the housing includes an undulating surface.

In some embodiments, the dispenser further includes a spool, the dental floss being on the spool.

In another aspect, the invention features a floss dispenser that includes a) a housing that includes an exit for floss, b) a floss carrier disposed in the housing, the floss carrier including a member extending from the floss carrier to inhibit the movement of a strand of floss to a point outside of the exit, and c) a strand of dental floss on the floss carrier, the strand of floss extending through the exit. In one embodiment, the housing includes a first wall joined to a second wall, and the member inhibits the floss from moving between the first wall and the second wall. In some embodiments, the member inhibits movement of the floss from between the housing and the carrier.

In other aspects, the invention features a method of loading an above-described floss dispenser. The method includes passing the strand of floss around the arm to the exit. In one embodiment, the floss includes a powder coating.

In another aspect, the invention features a method of dispensing dental floss from a floss dispenser that includes a) a housing that includes an exit for floss, b) a floss carrier disposed in the housing, the floss carrier including an arm extending across the exit, and c) a strand of dental floss on the floss carrier, the strand of dental floss extending through the exit. The method includes pulling a strand of dental floss through the exit. In one embodiment, the floss exhibits smooth unwind. In other embodiments, the floss includes a powder coating. In another embodiment, the housing is substantially free of entangled floss after dispensing a portion of the floss.

The retaining arm of the floss dispenser provides a mechanism by which a strand of dental floss is maintained in the exit hole of the dispenser. The retaining arm thus prevents the strand of dental floss from slipping between the various parts of the dispenser (e.g., between the floss carrier and one or more walls of the dispenser). The retaining arm also prevents the strand of floss from becoming snagged on the housing. The nonreturn loading mechanism facilitates the process of loading (i.e., positioning) the floss in the exit, yet inhibits the floss from leaving the exit. The dispenser also features a breaking mechanism that prevents the strand of floss from unwinding so rapidly that unwound floss accumulates or becomes entangled in the housing of the dispenser.

The dispenser also enables smooth unwind of the floss in dispensers in which the housing has a non-smooth interior surface. The dispenser is particularly well suited to the smooth, tangle free unwind of powder-coated dental floss.

Other features and advantages of the invention will be apparent from the following description of the preferred embodiments thereof and from the claims.

DETAILED DESCRIPTION

Figure 1:
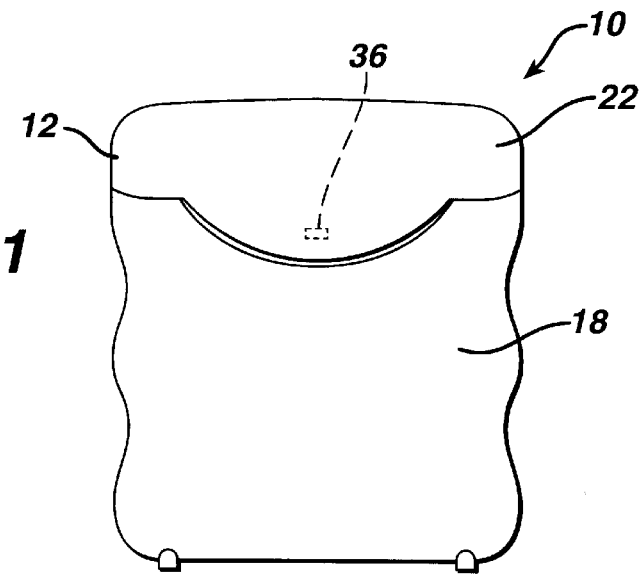
FIG. 1 is a plan view of the front of a floss dispenser.
Figure 2:
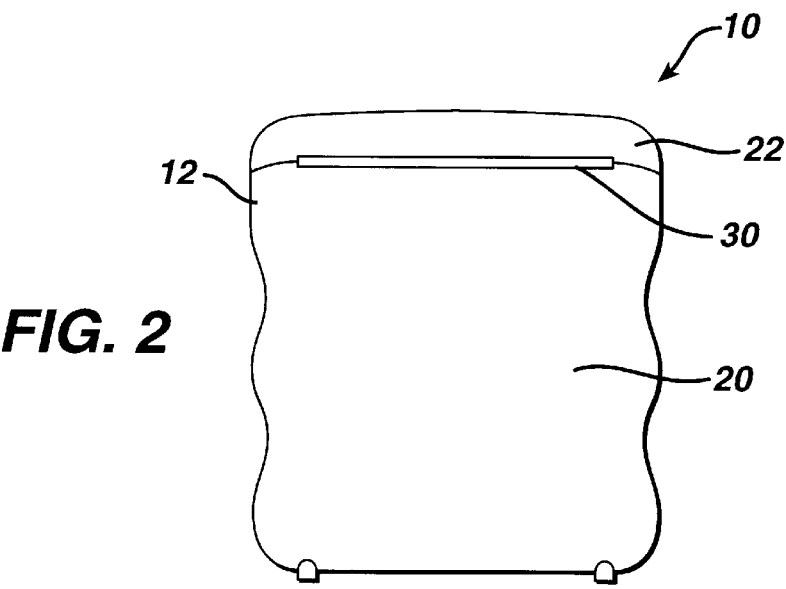
FIG. 2 is a plan view of the back of the floss dispenser of FIG. 1.
Figure 3:
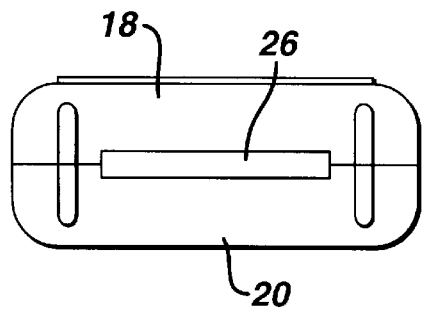
FIG. 3 is a plan view of the bottom of the floss dispenser of FIG. 1.
Figure 4:
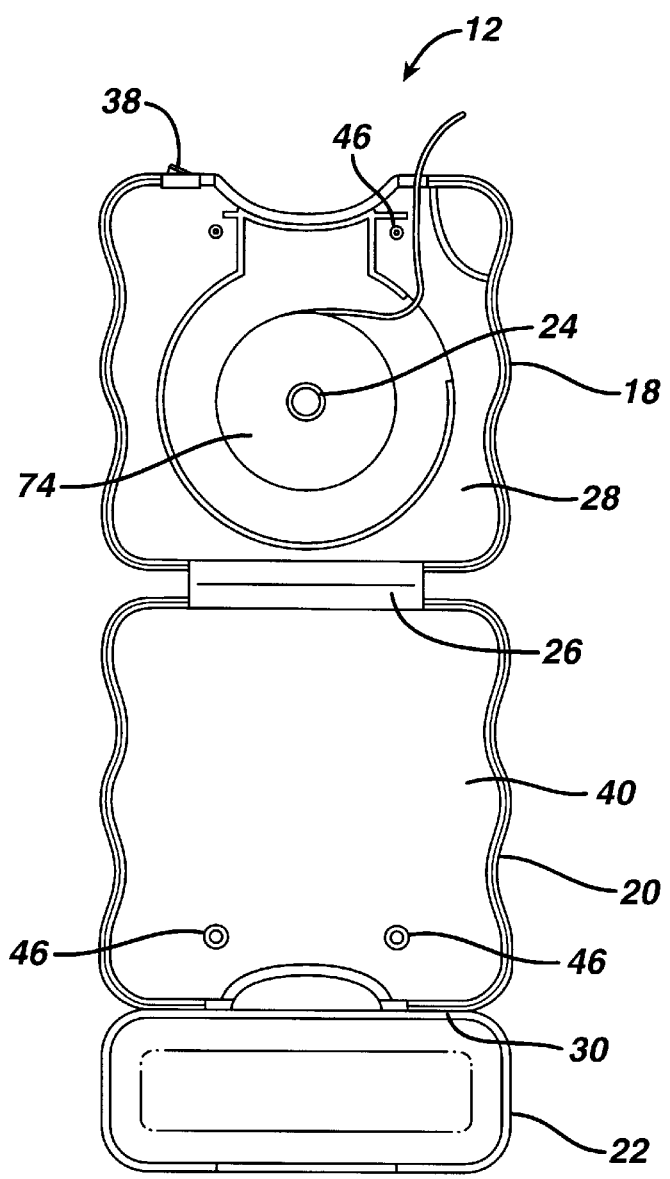
FIG. 4 is a plan view of the interior of an unassembled unitary housing of the floss dispenser of FIG. 1.
Figure 5:
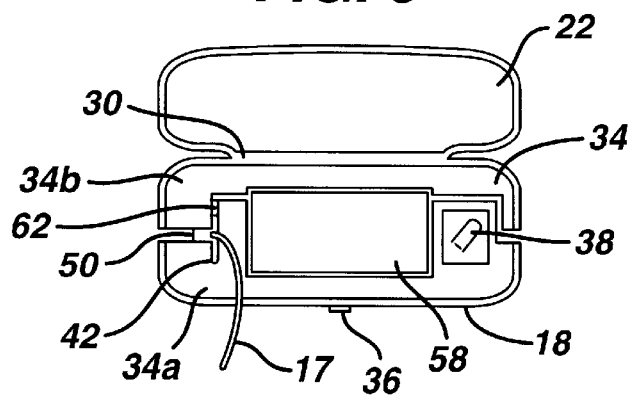
FIG. 5 is a plan view of the floss dispensing surface of the floss dispenser of FIG. 1.
Figure 6:
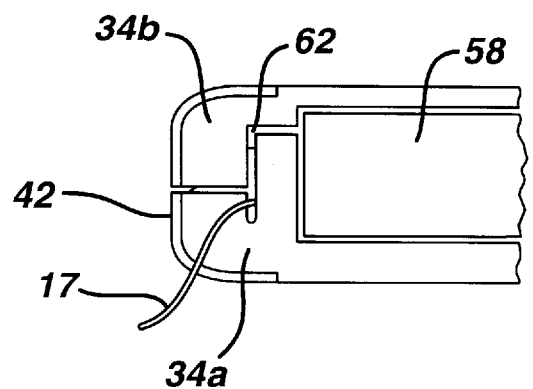
FIG. 6 is an enlarged view of a portion of the floss dispensing surface of FIG. 5.
Figure 7:
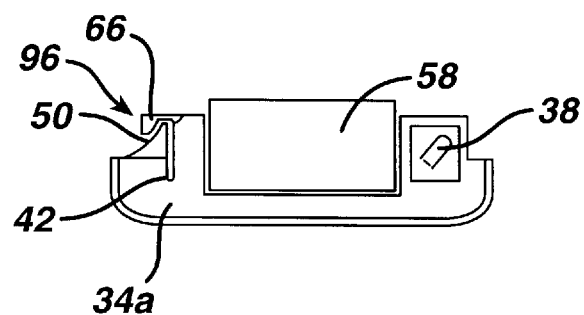
FIG. 7 is a plan view of the floss dispensing surface of FIG. 4 with half of the housing removed.
Figure 8:
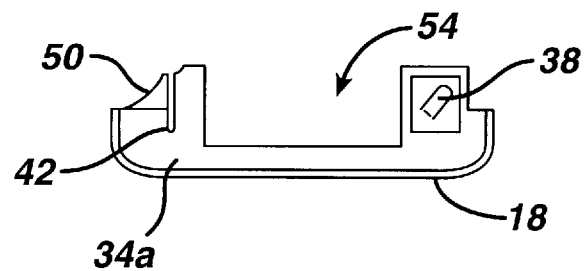
FIG. 8 is a view of the floss dispensing surface of FIG. 7 with the floss carrier removed.
Figure 9:
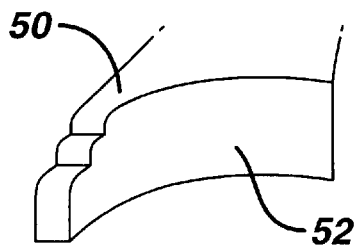
FIG. 9 is an enlarged view of the finger of the housing of the floss dispensing surface of FIG. 7.
Figure 10:
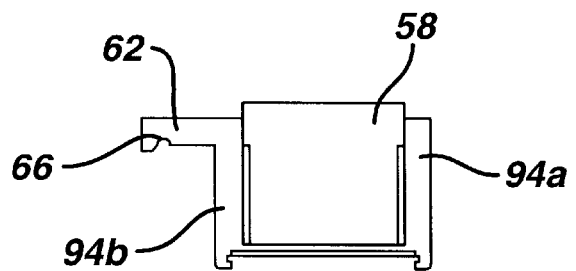
FIG. 10 is a plan view of the saddle of the floss carrier of the floss dispenser of FIG. 1.
Figure 11:
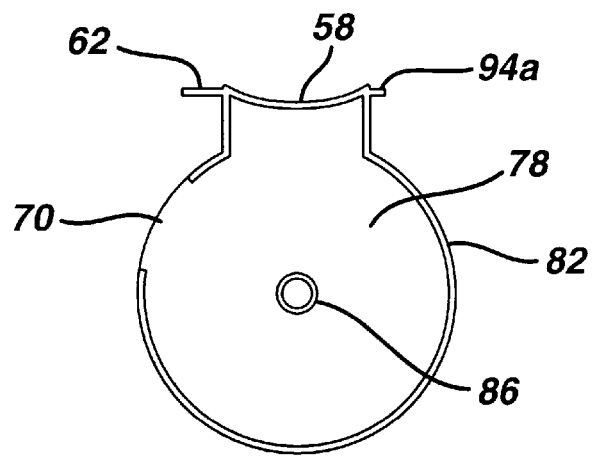
FIG. 11 is a plan view of the back of a floss carrier of the dispenser of FIG. 1.
Figure 12:
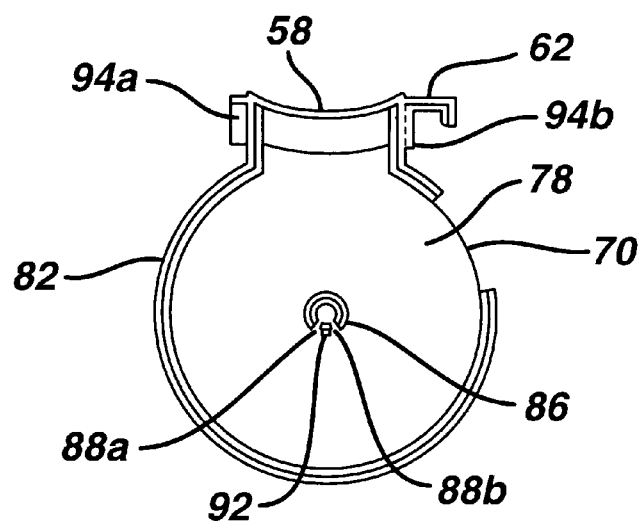
FIG. 12 is a perspective view of the spool receiving side of the floss carrier of FIG. 11.
Figure 13:
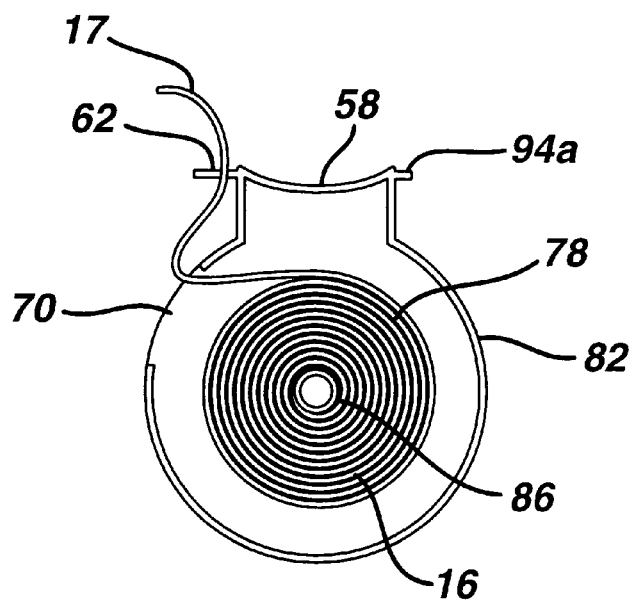
FIG. 13 is a plan view of the back of the floss carrier of FIG. 10 loaded with a spool of dental floss.

Referring to the Figures, the dental floss dispenser 10 includes a housing 12, a floss carrier 14 disposed in the housing 12, and a spool 74 of dental floss 17 on the carrier 14.

The housing 12 includes a front section 18, a back section 20, and a cover 22. The interior and exterior surfaces of the front 18 and back sections 20 can be planar or nonplanar, and preferably have an undulating (i.e., wavelike) appearance. Preferably a spindle 24 extends from the interior surface 28 of the front section 18 of the housing 12. The interior surface 28 of the front section 18, and the interior surface 40 of the back section 20 include guiding lock mechanisms 46 that guide the alignment of the front 18 and back sections 20 and lock the two sections together to form the housing 12 of the dispenser 10.

The housing 12 is preferably a unitary plastic housing such that the front section 18, back section 20 and cover 22 are one article. Unitary plastic housings can be formed by a molding process, preferably an injection molding process where a molten thermoplastic polymer is injected into a cavity of a mold thereby forming the molded unitary plastic housing. The thermoplastic polymer can be any plastic polymer and preferably is a plastic capable of producing a "living hinge." A "living hinge" is an area in a molded plastic part that enables the molded plastic part to fold along a crease line thereby forming a hinge. Preferably the thermoplastic polymer is polypropylene.

The unitary housing 10 includes a first hinge 26 interposed between the front section 18 and back section 20. When the front section 18 is folded along the first hinge 26 toward the back section 20 an enclosure for holding a spool 74 of floss is formed. Preferably the first hinge 26 is a "living hinge." A second hinge 30, preferably a living hinge, is interposed between the cover 22 and the back section 20 such that the cover 22 can fold along the second hinge 30 toward the floss dispensing surface 32 formed by the union of the back section 20 and the front section 18. The interior surface of the cover 22 includes a recess (not shown) for receiving catch 36 provided on the exterior surface of front section 18. The cover 22 mates with the catch 36 such that the cover 22 is secured in a closed position until a user releases the cover 22 from the catch 36 and opens the dispenser 10.

The floss dispensing surface 32 includes a floss exit 42 through which a strand of floss 17 passes from the interior of the housing 12 to the exterior of the housing 12. The floss exit 42 is defined by the union of two halves 34a, 34b of the top wall 34. A finger 50 extends from one half 34a of the top wall 34 at a level that is lower that second half 34b of the top wall 34 such that when the housing 12 is closed, i.e., the two halves 18, 20 of the housing 12 come together to define the exit 42, the finger 42 extends under the second half 34a of the top wall 42. The tip of the finger 50 is tapered to facilitate loading of the strand of floss 17 in the exit 42. The finger 50 is preferably triangular in shape and includes a swooping edge 52, which guides the strand of floss 17 when loading the floss 17 in the exit 42.

The floss dispensing surface 32 also includes a cutter 38 for severing the strand of floss 17 after the desired amount of floss 17 has been dispensed. The cutter 38 can also catch the strand of floss 17 after it has been cut such that the strand of floss 17 remains lodged in the cutter 38 until subsequent use. An opening 54 for receiving a portion of the floss carrier 14 is disposed between the floss exit 42 and the cutter 38.

The floss carrier 14 includes a back wall 78, a spindle 86, a side wall 82, a saddle 58, and a retaining arm 62 extending from the saddle 58. The back wall 78 is preferably substantially smooth and the spindle 86 extends at a right angle to the back wall 78. The spindle 86 has an interior diameter of sufficient dimension such that the spindle 86 can sit on the spindle 24 of the housing 12. The side wall 82 extends at a right angle to the circumferential edge of the back wall 78. The side wall 82 helps maintain the floss 17 in the area defined by the spool 16 and the side wall 82. The side wall 82 also inhibits over-unwind and prevents excess floss 17 from accumulating or becoming entangled within the housing 12. The side wall 82 includes an opening 70 through which the strand of floss 17 exits the floss carrier 14.

The spindle 86 of the carrier 14 includes two slits 88a and 88b defining a central region 90 and a breaking mechanism 92 positioned toward the spool receiving end of the spindle 86. The breaking mechanism 92 slows the rotation of the spool of floss 16 during unwind. When the floss carrier 14 is in position in the housing 12, the spindle 86 of the floss carrier 14 preferably rests on the spindle 24 of the housing 12. The mating of the two spindles 24, 86 assists in further stabilizing the carrier 14 in the housing 12.

The floss carrier 14 is positioned in the housing by sliding the saddle 58 portion of the floss carrier 14 into opening 54. Two guides 94a, 94b extend from the saddle 58 and help guide the floss carrier 14 into position in the opening 54 and maintain the floss carrier 14 in position in the housing 12.

A floss retaining arm 62 extends from the saddle 58 past the floss exit 42. The floss retaining arm 62 forms an end wall of the exit 42 and maintains the strand of floss 17 within the exit 42. The floss retaining arm 62 is positioned in the housing 12 such that it prevents the floss 17 from slipping out of the exit 42 or from being pulled outside of the exit 42 (e.g., between the front 18 and back sections 20, or between the floss carrier 14 (e.g., the saddle 58) and the front section 18 or the back section 20 of the housing) when the strand of floss 17 is pulled by a user and unwound from the spool of floss 16.

The retaining arm 62 preferably includes an elbow 66. The elbow 66 and finger 50 of the housing 12 combine to form a nonreturn loading mechanism 96. The nonreturn loading mechanism 96 facilitates loading of the strand of floss 17 in the exit 42, yet inhibits the floss 17 from slipping out of the exit 42 and becoming lodged between the walls 18, 20 and 34a–b of the housing 12. Preferably a portion of the retaining arm 62 is relatively closer to finger 50 near exit 42 side of finger 50 and relatively farther from finger 50 at the swooping surface 52 of finger 50.

It is preferable that the floss carrier 14 and, in particular, the saddle 58, be made from a transparent material, e.g., glass or plastic, so that the amount of floss 17 remaining on the spool 74 of floss can be observed through the saddle 58. Preferably the saddle 58 exhibits a color (e.g., blue, green or pink) that is different from the color (e.g., white) of the housing 12.

A spool of floss 16 is placed on spindle 86 of the floss carrier 14 and a strand of the floss is fed through opening 70, around retaining arm 62 and along the swooping surface 52 of finger 50, between the tapered end of finger 50 and elbow 66, and into exit 42. The housing 12 is then closed (e.g., by snapping the components together) to form the dispenser 10. A user can then pull on the strand of floss 17, which causes the spool 74 to rotate and the floss 17 to dispense. The spool 74 of floss preferably exhibits smooth unwind (i.e., it is substantially free from jerking, e.g., intervals of slower and faster unwind) as it rotates around the spindle 86 during dispensing.

A variety of dental flosses can be dispensed from the floss dispenser including, e.g., multifilament dental floss, monofilament dental floss, dental floss that includes a coating, e.g., wax, powder, flavor, scent and combinations thereof, dental tape, bulked dental floss, woven dental floss and combinations thereof.

Other embodiments are within the claims.

What is claimed is:

1. A floss dispenser comprising:
    a) a housing comprising an exit for floss;
    b) a floss carrier disposed in said housing, said floss carrier comprising an arm extending across said exit, said arm defining a portion of said exit; and
    c) a strand of dental floss on said floss carrier, said strand extending through said exit.
2. The dispenser of claim 1, wherein said arm is positioned to maintain a strand of floss in said exit.
3. The dispenser of claim 1, wherein said arm comprises an elbow.
4. The dispenser of claim 1, wherein said housing further comprises a finger extending from said housing toward said arm.
5. The dispenser of claim 4, wherein said finger comprises a tapered surface.
6. The dispenser of claim 4, wherein said finger is triangular in shape.
7. The dispenser of claim 1, further comprising a nonreturn loading mechanism.
8. The dispenser of claim 7, wherein said nonreturn loading mechanism comprises said arm and a finger extending from said housing toward said arm.
9. The dispenser of claim 8, wherein said arm and said finger are positioned to facilitate the loading of a strand of floss in the exit and to inhibit the strand of floss from leaving the exit.
10. The dispenser of claim 8, wherein said arm comprises an elbow and said finger extends toward said elbow.
11. The dispenser of claim 1, further comprising a spool, said dental floss being on said spool.
12. The dispenser of claim 1, wherein said housing comprises a unitary housing.
13. The dispenser of claim 1, wherein said housing comprises a spindle and said floss carrier is disposed on said spindle.
14. The dispenser of claim 1, wherein said housing further comprises a cutter and an opening disposed between said exit and said cutter, and a portion of said floss carrier is positioned in said opening.
15. The dispenser of claim 1, wherein said carrier comprises a back wall and an arcuate side wall extending from said back wall.
16. The dispenser of claim 15, wherein said arcuate side wall includes an opening.
17. The dispenser of claim 15, wherein said back wall is substantially smooth.
18. A floss dispenser comprising:
    a) a housing comprising an exit for floss;
    b) a floss carrier disposed in said housing, said floss carrier comprising a member extending from said floss carrier to inhibit the movement of a strand of floss to a point outside of said exit; and
    c) a strand of dental floss on said floss carrier, said strand extending through said exit, said housing comprising a first wall joined to a second wall, said member inhibiting said floss from moving between said first wall and said second wall.
19. The dispenser of claim 18, wherein said member inhibits movement of said floss from between said housing and said carrier.

* * * * *